United States Patent
Patell et al.

(10) Patent No.: US 8,030,543 B2
(45) Date of Patent: Oct. 4, 2011

(54) EFFICIENT TRANSFORMATION METHOD FOR SUNFLOWER AND OIL SEEDS BASED ON POSITIVE SELECTION

(75) Inventors: Villoo Morawala Patell, Karnataka (IN); Rajyashri Ramakrishna Karur, Karnataka (IN)

(73) Assignee: Avesthagen Limited, Bangalore, Karnataka (IN)

( * ) Notice: Subject to any disclaimer, the term of this patent is extended or adjusted under 35 U.S.C. 154(b) by 219 days.

(21) Appl. No.: 12/087,208

(22) PCT Filed: Jan. 12, 2006

(86) PCT No.: PCT/IB2006/000491
§ 371 (c)(1),
(2), (4) Date: Jun. 26, 2008

(87) PCT Pub. No.: WO2007/080440
PCT Pub. Date: Jul. 19, 2007

(65) Prior Publication Data
US 2009/0288230 A1    Nov. 19, 2009

(51) Int. Cl.
*C12N 15/82* (2006.01)
*C12N 15/63* (2006.01)
*C12N 15/00* (2006.01)

(52) U.S. Cl. ........ 800/288; 800/278; 800/284; 800/290; 435/320.1; 435/468

(58) Field of Classification Search ........................ None
See application file for complete search history.

(56) References Cited

U.S. PATENT DOCUMENTS 5,767,378 A * 6/1998 Bojsen et al. .............. 800/317.2

FOREIGN PATENT DOCUMENTS

WO    WO-94/20627 A    9/1994
WO    WO-96/24667 A    8/1996

OTHER PUBLICATIONS

Haldrup, A. et al: "The xylose isomerase gene from Thermoanaerobacterium thermosulfurogenes allows effective selection of transgenic plant cells using D-xyloe as the selection agent" Plant Molecular Biology, Nijhoff/Junk, The Hague, NL, vol. 37, May 1998, pp. 287-296, XP002129151, ISSN: 0167-4412.
Sankara Rao K et al: "Agrobacterium-Mediated Transformation of Sunflower (*Helianthus annuus* L.) A Simple Protocol", Annals of Botany, Academic Press, London, GB, vol. 83, No. 4, 1999, pp. 347-354, XP002953938, ISSN: 0305-7364.

* cited by examiner

*Primary Examiner* — Brent T Page
(74) *Attorney, Agent, or Firm* — Hamre, Schumann, Mueller & Larson, P.C.

(57) ABSTRACT

The invention describes a highly improved, reproducible and a consistent method of transformation and regeneration that results in obtaining 12-15% transgenic plants. The present invention relates to a method of selecting genetically transformed Sunflower explants based on their ability to utilize Xylose as a sole carbohydrate source. Further disclosed is the nucleic acid sequence of the Xylose Isomerase gene, vector construction for incorporation of the selection marker gene and the process of *Agrobacterium* Mediated Transformation of target host plant with the vector comprising the gene encoding the enzyme Xylose isomerase under the functional combination of the heterologous regulatory sequences. Also disclosed is the method of selecting the putative transformants post transformation with the said vector that possess a metabolic advantage of utilizing Xylose as a sole carbon source. Increased efficiency of regeneration, better growth and survival has been observed on subjection to the described method of positive selection. The subject invention alleviates the disadvantages of negative selection methods such as the undesired elimination of the transformed cells and the potential environmental harm caused due to the dispersal of the antibiotic and the herbicide resistant genes.

12 Claims, 10 Drawing Sheets

Presence of the complete Xylose isomerase domain in the 1.5kb sequence of SC-1 desaturase

Fig- 2 gnl|CDD|7536, pfam00259, Xylose isomerase
         CD-Length = 411 residues, 100.0% aligned
         Score = 465 bits (1198), Expect = 5e-132

```
Query:  29   PDEEILGKKMKDWLKFSVCFWHTFRSVGMDPFGKPTITRPQGDDGSDSVENALPRVDAA   88
Sbjct:  1    PEEVILGKTMEEHLRFSFGYWHTFWQDGKDPFGDATPERPWNKYTDMDL---ALDPVEAV  57

Query:  89   FELPTKLGVEYYSPHDVDVSPEGATLKETRENLDKITDPMLELQKRTCVKLLWGTANLFT  148
Sbjct:  58   FEPAEKGNAYGFCFHDVDLAPEGASLRERNKMLDKIVDRFKEALDETGLKVLWGTANLFT  117

Query:  149  NPRYMNGGSTNPDPNVFIRAAAQVKKAIDVTHKLGGQGFVFWGGREGYMHILNTDVVREM  208
Sbjct:  118  HPRFKDGAATSPDADVFAYAAAKVKKAMELAKRLGAENYVFWGGREGYETLLNTDLRAEL  177

Query:  209  NSYAQMLKMAIAYKKKIGFDGQILVEPKPREPMKHQYDYDVQTVIGFLREHGLEKEVLLN  268
Sbjct:  178  DRLAEFLDMAVEYAKEIGYDGRFLIEPKPNEPTGHQYDPDVATALAFLKQLDLPELFKLN  237

Query:  269  VEPNHETLAGHEFEHGFLFAAKLGMLGSIDANTGSESLGWDTDEFITDQTRATLLCRTII  328
Sbjct:  238  IEANHATLAGHNFQHEIAQALMAGKLGSIDANQGDRLLGWDTDLFPTGVLETTLAMYEIL  297

Query:  329  EMGGFKKGGLNFDAKVRRSSTDPEDLFTAHVASMDALAKGLPNAAKLVDEGRMAKMLAER  388
Sbjct:  298  ENGGFTGGCLNFDAKPRRQSEDPEDLFASHIAGMDTYALLKKRAAAFREDPEVQEALAEP  357

Query:  389  YAGWDSGLGKRIEDGQSSLDELEEHALQNDEE---PAKTSAKQEKFIAVLNQYI  439
Sbjct:  358  YVSENSGIGLDIVEGKADLKALEAYAKEKDLDAAAKGQSGFQELLQLAINRYL  411
```

Homology of the motif from SC-1 to the Xylose isomerase domain

Map of pGEX-XI

Induction of Xylose Isomerase in E.coli.

A: Amplification of the ORF from the Xylose Isomerase clone.
B: Restriction of the pCAMBIA-XI with Xho I Sequence of full length Codon optimized Xylose Isomerase transcript of SC-1 in frame in pCAMBIA Vector and replacement of hpt with XI in pCAMBIA-CO-XI.

Sunflower SEA explants A) cultured on sucrose (35gm/l) B) cultured on D-Xylose (30gm/l) C) cultured on medium without any carbon source.

A                                                                B

Budding as observed in transformed SEA explants cultured on A) Hygromycin
(25mg/l) and B) Xylose (15g/l)+Sucrose (5gm/l) after 2 weeks of selection A) SEA Explants on I$^{st}$ Selection Media. B) & C) Elongation Media D) Rooting Media E) & F) Plantlets in Hardening stage.

Amplification of transformed SEA explants with XI primers.

EFFICIENT TRANSFORMATION METHOD FOR SUNFLOWER AND OIL SEEDS BASED ON POSITIVE SELECTION

FIELD OF INVENTION

*Helianthus annuus*, or sunflower, is a recalcitrant species, which is extremely difficult to transform. We report a highly improved method of transformation, which results in 2-3 fold greater increase in the number of transformants obtained as against the cited prior art. The present invention relates to a method of selecting genetically transformed Sunflower explants based on their ability to utilize Xylose as a sole carbohydrate source. Further disclosed is the nucleic acid sequence of the Xylose Isomerase gene, vector construction for incorporation of the selection marker gene and the process of *Agrobacterium* Mediated Transformation of target host plant with the vector comprising the gene encoding the enzyme Xylose isomerase under the control of heterologous regulatory sequences. Also disclosed is the method of selecting the putative transformants post transformation with the said vector that possess a metabolic advantage of utilizing Xylose as a sole carbon source. Increased efficiency of regeneration, better growth and survival has been observed on subjection to the described method of positive selection. The subject invention alleviates the disadvantages of negative selection methods such as the use of antibiotic or herbicide resistance genes.

BACKGROUND OF INVENTION

Plant transformation is now a core research tool in plant biology and a practical tool for cultivar improvement; transformation of several plant species via *Agrobacterium* mediated transformation has become a routine technology. Sunflower is a major crop used worldwide for the production of edible oils; attempts to transform the species are being made for a number of decades—however, the sunflower is a recalcitrant species resistant to the methods of transformation used so far. Attempts to transform the species using *Agrobacterium* or biolistic methods, using different selectable markers have resulted in very low transformation efficiencies ranging from 0.6-6%.

When a population of plant cells is transformed, selection of the transformed cells is typically done using a selection marker. The major technical challenge in plant transformation is the development of selection markers for screening and selection of successfully transformed cells. This process of selection is extremely important, with the cost of screening for transformants sometimes exceeding the costs of transformation itself. The choice of the selectable marker gene, the selective agent, its concentration and the timing of the application is very important for a strict selection of transformed cells. On the other hand, regeneration should not be impeded. Hence though a strict selection regime is desirable, this should not impede the development potential of the transformants. The choice of conditions that rightly balances the two needs constitutes an art in itself.

Selectable markers identified today can be differentiated into two types that enable transgenic plants or cells to be identified after transformation. They can be divided into positive and negative markers conferring a selective advantage or disadvantage respectively. Negative selectable markers are those, which allow the selection of transformed cells, or tissue explants by their ability to grow in the presence of an antibiotic or herbicide. In addition to selecting of transformants, such markers can be used to follow the inheritance of a foreign gene in segregating population of plants.

These negative selection methods have considerable disadvantages. The most significant of them all is that the non-transformed cells are killed in the presence of the phyto-toxic product and in cases where a coherent tissue is used there is a risk that the transformed cells also die, due to the fact that the death of the non-transformed cells may cut off the supply of nutrients to the transformed cells or because of the damaged or dying non-transformed cells may excrete toxic compounds. Moreover the presence of an antibiotic resistance gene in ingested plants is a matter of concern. In addition, selection of cells or tissues using negative selection requires precise timing of expression of the introduced genes in relation to the selection process. If the transgenic cells are treated with a toxic compound before the detoxifying gene is expressed or before enough of the gene product is produced to ameliorate the action of the toxic compound, both the transgenic and the non-transgenic cells are killed. If selection is delayed, the selection of transgenic cells or tissues may be hindered by, for example, shoot or callus formation from non-transgenic cells or tissues, which forms a barrier to the penetration of the compound used to select the transformed cells.

The above-mentioned disadvantages are overcome to a substantial extent, by the method of positive selection whose operating principle is converse to negative selection. Rather than conferring resistance to a negative or toxic substance, positive selection involves conferring onto the transformed cell a metabolic, or other competitive advantage over non-transformed cells. These identify and select the genetically transformed cells without damaging or killing the non-transformed cells in the population.

Sunflower is an important oil-seed crop, which is reported to be recalcitrant to transformation and regeneration (Schrammeijer et al., Plant Cell Reports, 1990 9:55-60). Schrammeijer et al., have evaluated some of the potential problems with the regeneration from various explants of Sunflower, the transformants being selected by their ability to grow on negative selection based agents. Kanamycin and hygromycin are the most widely used selection agents for sunflower transformation although these are known to be detrimental to their organogenic potential (Everett et al., 1987; Muller et al., 2001).

Disclosed in this invention is a novel method of selecting transformants belonging to the species *Helianthus annuus*, specifically exemplifying a positive selection method that involves conferring to the transformed tissue explants an ability to metabolize certain compounds preferably Xylose; transformed explants are selected by simply culturing them on a medium containing the referred selection agent.

The method of selection disclosed herein relates to a method of screening and selecting suitable transformed explants for regeneration. A stable, precise, higher transformation and regeneration efficiency has been achieved through our method. The advantages of the technology described are lucid enough to distinguish it from the existing technologies.

SUMMARY OF THE INVENTION

Sunflower is a major crop used worldwide for the production of edible oils. Attempts to transform the species using *Agrobacterium* or biolistic methods, using different selectable markers have resulted in very low transformation efficiencies ranging from 0.6-6%. This invention describes a highly improved, reproducible and consistent method of transformation and regeneration that results in obtaining 12-15% transgenic plants.

This invention relates to a positive selection method that confers transformed explants of species *Helianthus annuus* an ability to metabolize Xylose. One aspect of the invention pertains to construction of the vector construct comprising a selectable marker gene. A specific aspect pertains to the *Agrobacterium* mediated method of transforming the constructed vector comprising the selectable marker gene into the host plant explants under conditions suitable for infection. The successfully transformed cells comprising the gene of interest are induced with a positive effect that gives these cells a selective metabolic advantage over the non-transformed cells when cultured together on a suitable medium containing the selective agent. This selective advantage is attributed to the successful expression of the marker gene in the presence of the marker compound.

According to a further aspect the selectable marker compound supplied to the population of the transformed tissues is Xylose that induces the expression of the marker gene in the transformed explants.

Further still, an additional aspect of the subject invention pertains to the polynucleotide molecule that encodes the protein having the biological activity of Xylose Isomerase. Specifically, the aspect pertains to a polynucleotide as represented in SEQ ID 3.

Moreover, the transformation efficiency achieved from the disclosed method is 12-15% and the regeneration efficiency has been proven to be 2-3 fold greater than antibiotic (hygromycin) based methods of negative selection.

PRIOR ART

U.S. Pat. No. 5,767,378 titled "Mannose or Xylose positive selection" relates to a method of identifying or selecting from a population of eukaryotic cells cultivated on or in a medium containing at least one compound, cells which have a metabolic advantage as a result of being transformed. Wherein the cells are being transformed with a nucleotide sequence or a co-introduced nucleotide sequence which when expressed results in the metabolism of compounds like mannose or xylose.

Haldrup et al. (1998), have established that the xylose isomerase gene from *Thermonanaerobacterium thermosulfurogenes* allows effective selection of transgenic plants using D-xylose as the selection agent (Plant Molecular Biology (1998), 37(2), 287-296) in potato, tomato and tobacco species. The xylose isomerase gene was transferred to the target plant by *Agrobacterium*-mediated transformation. Selection studies showed that in potato and tomato, the xylose isomerase selection was more efficient than the kanamycin resistance selection, whereas in the tobacco plants the opposite effect was observed.

A recent review titled "Positive selection marker genes for routine plant transformation" mentions that the selectable marker genes used so far have been either antibiotic resistance genes or herbicide tolerance genes. It also describes the new classes of marker genes that are confer a metabolic advantage of the transgenic cells over the non-transformed cells.

Haldrup et al. (2001), describe the selection of transformed plants based on the use of Xylose Isomerase as the selection marker (In Vitro Cellular & Developmental Biology: Plant (2001), 37(2), 114-119.

A continuation part of the U.S. Pat. No. 5,767,378 further relates to novel glucuronide compounds including cytokinin glucuronide compounds for use in a method of selecting genetically transformed cells from a population of cells comprising introducing a desired nucleotide sequence or the co-introduced nucleotide sequence into the genome of a cell whereby the desired nucleotide sequence induces a positive effect by giving the transformed cells a competitive advantage when the population of cells are supplied with an inactive compound thereby allowing the transformed cells to be identified from the population of non-transformed cells.

Hou et al describes the use of selectable marker genes in transgenic plants and its removal. The review focuses on the use of selective marker genes in transgenic plants and its removal with emphasis on positive selection markers in transgenic plants by using isopentenyl transferase gene, xylose isomerase gene, phosphomannose-isomerase gene and beta-glucuronidase gene. Also described are the methods of marker gene removal using cotransformation, site-specific recombination system, transposon-mediated reposition and homologous recombination.

The method of selection disclosed herein is lucid enough to distinguish from the prior art documents cited. Our invention specifically aims at the method of positive selection of transformed plant explants that belong to the plant species *Helianthus annuus*. Furthermore, the selectable marker gene that encodes for the protein Xylose isomerase has been isolated from the organism Schizochytrium and modified suitably for its expression in the host plant species. It has to be specifically noted that high transformation efficiency in Sunflower plants has been rarely reported. More specifically several problems have been noted with regeneration from various explant types of Sunflower (Schrammeijer et al., Plant Cell Reports, 1990 9:55-60)

We report a transformation efficiency and regeneration efficiency of 12-15%⁻—an efficiency that is 2-3 folds greater than that achieved so far.

B: Restriction of the pCAMBIA-XI with Xho I. Note the release of the hpt gene from the Xho I site.

Figure 6:
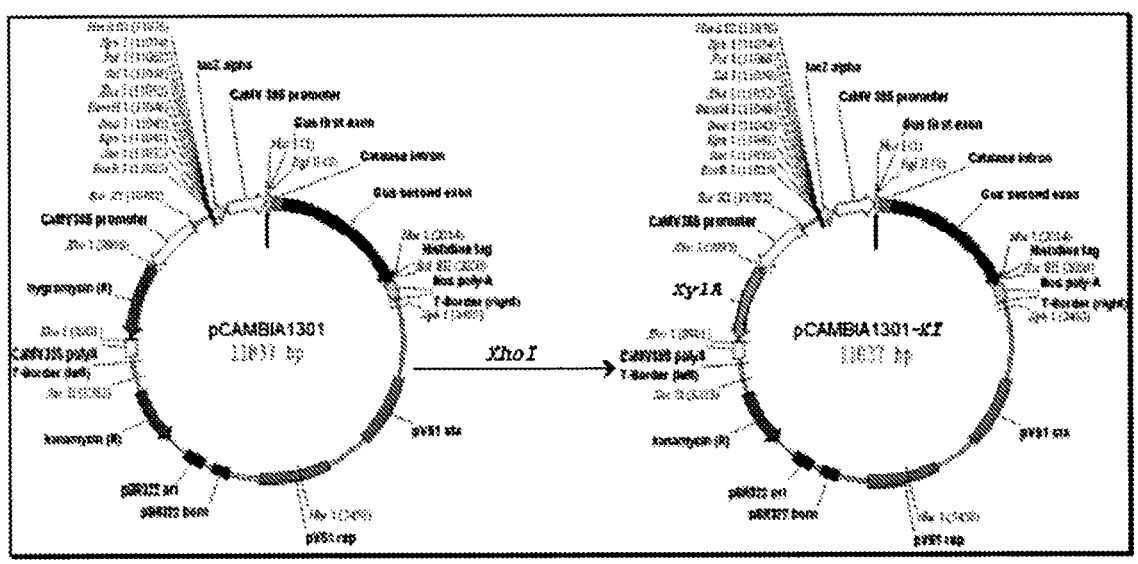

FIG. 6. Replacement of hpt with XI in pCAMBIA-CO-XI.

Figure 7:
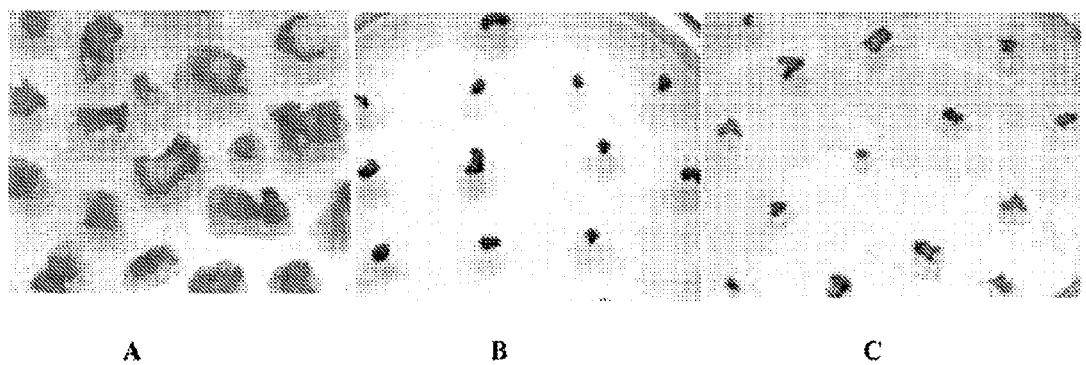

FIG. 7. Untransformed Sunflower SEA explants A) cultured on sucrose (35 gm/l) B) cultured on D-Xylose (30 gm/l) C) cultured on medium without any carbon source. The explants were photographed after 3 weeks.

Figure 8:
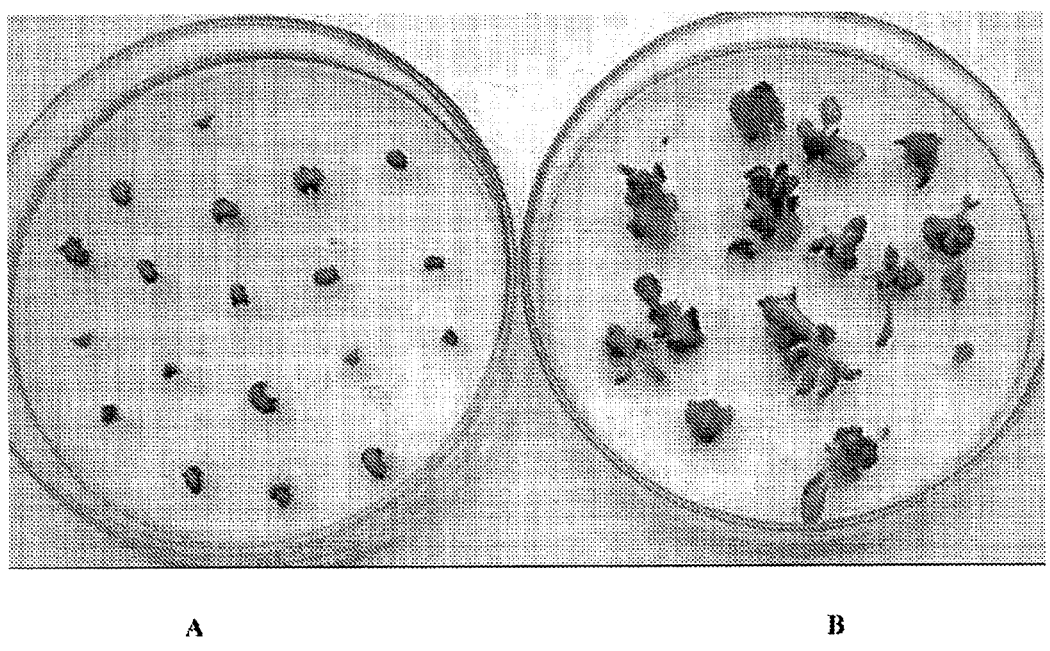

FIG. 8. Budding as observed in transformed SEA explants cultured on A) Hygromycin (25 mg/l) and B) Xylose (15 g/l)+Sucrose (5 gm/l) after 2 weeks of selection FIG. 9. A) SEA Explants on I$^{st}$ Selection Media. B) & C) Elongation Media D) Rooting Media E) & F) Plantlets in Hardening stage.

Figure 10:
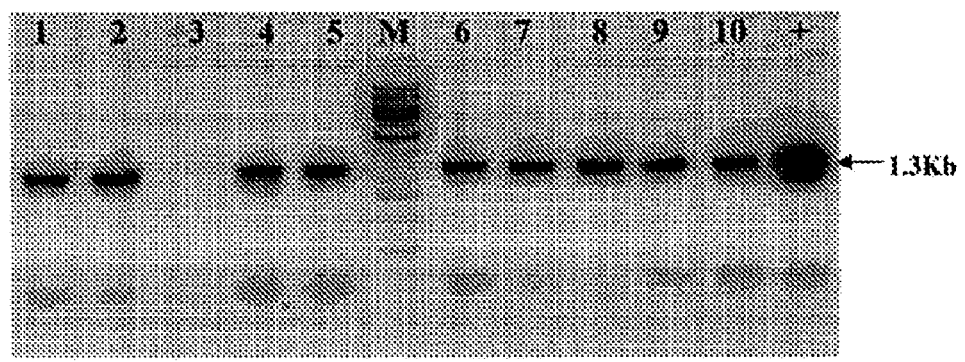

FIG. 10. Amplification of transformed SEA explants with XI primers.

BRIEF DESCRIPTION OF THE SEQUENCE LISTINGS

SEQ ID NO 1: Sequence of full length of Xylose isomerase transcript of SC1

SEQ ID NO 2: Translated Protein sequence of Xylose Isomerase of SC1

SEQ ID NO 3: Sequence of Xylose isomerase after optimization for expression in Plants SEQ ID NO 4: Sequence of full-length codon optimized Xylose isomerase transcript of SC1 in frame in pCAMBIA vector.

DETAILED DESCRIPTION OF THE INVENTION

The term "Selectable maker gene" refers to any nucleotide sequence that is preferably co-introduced with the gene of interest, wherein a selective advantage is conferred to a cell transformed with the said selectable marker gene.

The term "selective agent" is the compound or nutrient in inactive or precursor form which in the absence of, for example, expression of the selectable marker gene exists in a form substantially biologically inactive with respect to the cells in question, but which when the selectable marker is expressed or transcribed is hydrolyzed or otherwise activated or metabolized so as to provide the genetically transformed cells containing the gene of interest with a selective advantage and thereby allowing the cells to be selected.

The term "selective advantage" as used herein includes the terms selective, metabolic and physiological advantage and means the transformed cells are able to grow more quickly than the disadvantaged (non-transformed) cells, or are advantageously able to utilize substrates (such as nutrient precursors, etc.) which disadvantaged cells are not able to utilize.

Example: 1

Cloning of Xylose Isomerase from a Thraustochytrid Strain SC-1

Total RNA was isolated from three-day-old cultures of the Schizochytrium SC-1, a Thraustochytrid isolated from the backwaters of Goa. CDNA was synthesized from the mRNA using superscript Rnase (GibcoBRL). The cDNA was cloned into the NotI-SalI site of pSPORT1 vector and transformed into E. coli DH10B.

The primary cDNA library consists of 2×106 clones, while the amplified library has a titer of 2×1010 clones/ml. EST clones were randomly picked and inserts amplified with SP6 and T7 primers. The 5' ends of the 2000 cDNA clones were randomly selected and sequenced with T7 primers. 5' end sequencing of clones from the cDNA library of SC-1 led to the identification of cDNA clone of 1.5 kb which encodes a full-length Xylose Isomerase (xylA) cDNA of 1511 bp with a 5' UTR of 158 bp and a 3' UTR of 30 bp. It has an ORF of 1481 bp.

Figure 1:
FIG. 1. Complete Xylose isomerase domain in the 1.5 kb sequence of SC-1 desaturase FIG. 2. Homology of the motif from SC-1 to the Xylose isomerase domain FIG. 3. Map of pGEX-XI. The Xylose Isomerase gene was cloned between the BamHI and XhoI sites to study expression in *E. coli*.

The sequence of the CDS is given in the SEQ ID 1. It is the sequence of the full length Xylose Isomerase transcript of SC-1. The sequence translates into a protein of 440 amino acids. The amino acid sequence of the translated protein is represented in SEQ ID 2. The sequence shows 74% homology to the Xylose isomerase of *Arabidopsis thaliana*. It contains the complete Xylose isomerase domain and has been designated as the xylose isomerase of SC-1. Presence of the complete Xylose isomerase domain in the 1.5 kb sequence of SC-1 desaturase has been represented in the FIG. 1

FIG. 2 represents the homology of the motif from SC-1 to Xylose Isomerase domain.

Example: 2

Codon Optimization of the Xylose Isomerase

The xylose isomerase (xylA) sequence of SC-1 uses codons that are comparatively rarely used in plants; SC-1 predominantly utilizes CGC to code for Arginine where only 9% of the plant codons for Arg are CGC. Hence, the CGC codons were replaced with more frequently used codons for arginine. The clone was subjected to two rounds of multi-site directed mutagenesis for substituting 9 nucleotides prior to introduction into plants. The optimized sequence is represented in SEQ ID 3.

Example: 3

Cloning of Xylose Isomerase into pGEX Expression Vector

Figure 3:
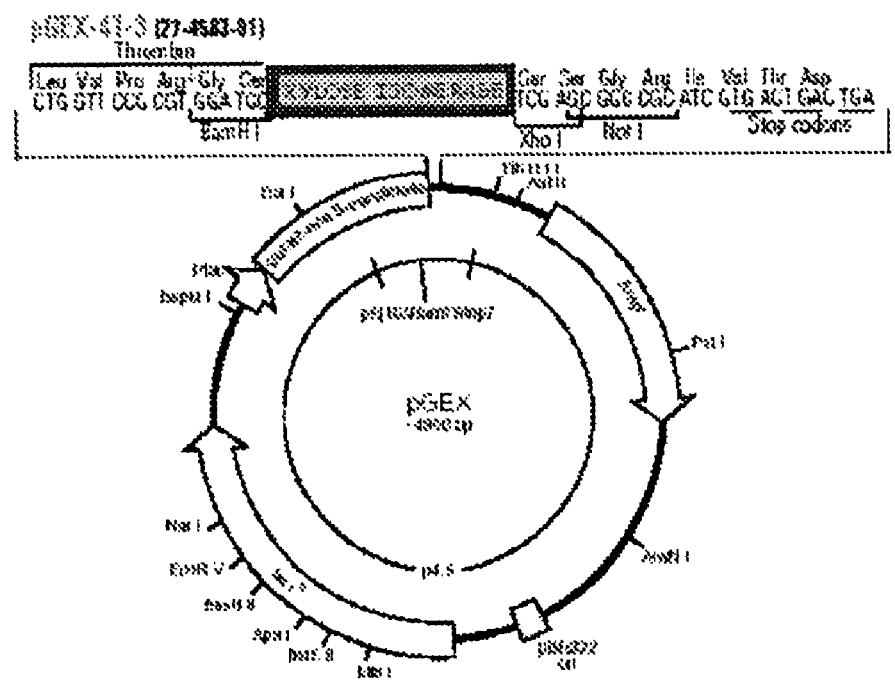

To confirm that the codon optimised gene does transcribe and translate, the codon optimized SC-1 XylA gene from pSPORT1, was amplified with the forward primer (5'GCGCGGATCCATGGGTGAATTCTTTC3') containing an BamHI site and the Reverse primer (5'GAAACTC-GAGCTTGTCGATTAAGAAATGTATTGGTT3') containing an XhoI site. The amplified PCR product (1323) was digested with BamHI and XhoI. pGEX4T-3 is an expression vector used to express the proteins as fusion proteins with the 26-kDa glutathione S-transferase (GST under control of the tac promoter. pGEX4T-3 was digested with BamHI and XhoI and the PCR product (restricted with BamHI and XhoI) cloned directionally between the two sites—the resultant clone was called pGEX-XI. Map of pGEX-XI has been represented in the FIG. 3

Expression of the Xylose Isomerase Fusion Protein in *E. coli*

Figure 4:
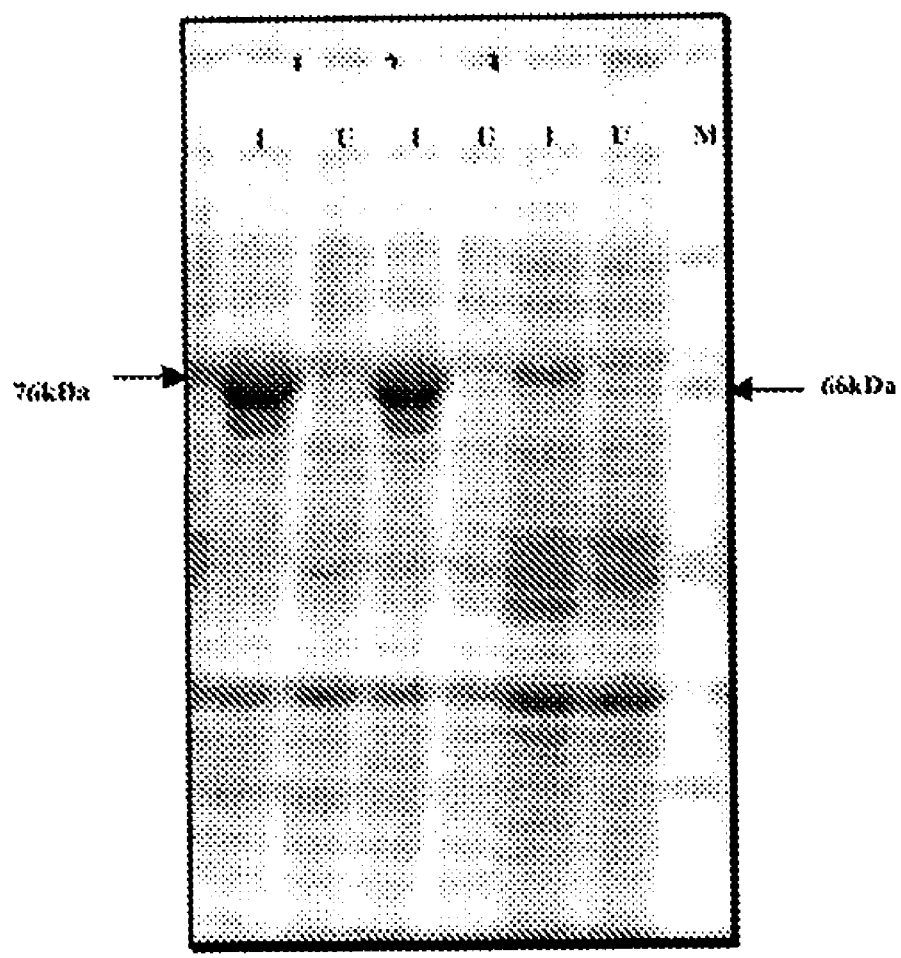
FIG. 4. Induction of Xylose isomerase in *E. coli*. Amplification of transformed SEA explants with XI primers. Lanes: I: Induced; U: Uninduced; 1,2,3: Different clones carrying the xylose isomerase gene; M: MW marker.

The pGEX-XI carrying the Xylose Isomerase gene was transformed into *E coli* BL21. The transformed cells were selected on LB media containing 100 µg/ml of Ampicillin. Colonies were picked up at random and were grown overnight in LB containing 100 ug/ml of ampicillin. 1% of these overnight cultures were used as starter cultures for inoculating 5 ml of LB broth containing 100 ug/ml of ampicillin. Cultures were incubated till O.D. 600 reached approximately 0.6-0.7. 2 ml each of these cultures was induced with 1 mM IPTG for 3 hrs. Simultaneously, 2 ml of the culture was pelleted down as control without induction. The cell pellets were resuspended in 100 µl sample buffer and 50 ul loaded onto a 10% SDS-PAGE gel. The induction is shown in the FIG. 4

A protein of 76 KDa, the expected size of the GST-Xylose isomerase fusion protein, was observed in the induced cells of clones 1 and 2 while being absent from the uninduced cells. Thus the codon optimized xylose isomerase is in the right reading frame and is capable of being transcribed and translated.

Proof of Function of Xylose Isomerase Gene in *E. coli*

The *E. coli* strain AB477 (proA2, his-4, aroC1, thi-1, lacY1, galK2, xyl-5, mtl-1, lambda⁻ supE44) is Xylose Isomerase (XylA) deficient (Haldrup et al., 1998 & 2001). The complementation of the Xylose Isomerase gene in the mutant will enable this strain to utilize and grow and thereby proving its function. E. coli strain AB477 was obtained from the E. coli Genetic Stock Center, USA. Xylose isomerase gene in pGEX4T-3 was transformed into competent cells of E. coli strain AB477 which was plated onto MacConkey agar plates containing 1% (w/v) D-Xylose with ampicillin (100 µg/ml). Transformants harboring the XylA gene were able to ferment D-Xylose and appear red on MacConkey agar plates containing xylose.

AB477 host cells, cells transformed with pGEX4T-3 and those transformed with pGEX-XI were plated onto MacConkey's media containing ampicillin (100 µg/ml) as well as media containing Xylose (1% w/v) and ampicillin (100 µg/ml) respectively. Red colonies were obtained with pGEX-XI in media containing xylose, while host cells and AB477 carrying pGEX4T3 did not grow in the media. Thus, the codon optimised xylose isomerase gene isolated from SC-1 is translated and functional.

Example: 4

Cloning of Xylose Isomerase into pCAMBIA

The pCAMBIA-1301 is derived from the pPZP vectors. The vector contains the hygromycin phospho-transferase (hpt) under the CaMV35S promoter and terminated by the CaMV35S polyA signal. The gene provides resistance to hygromycin so that transformed cells are selected for in hygromycin containing medium.

Figure 5:
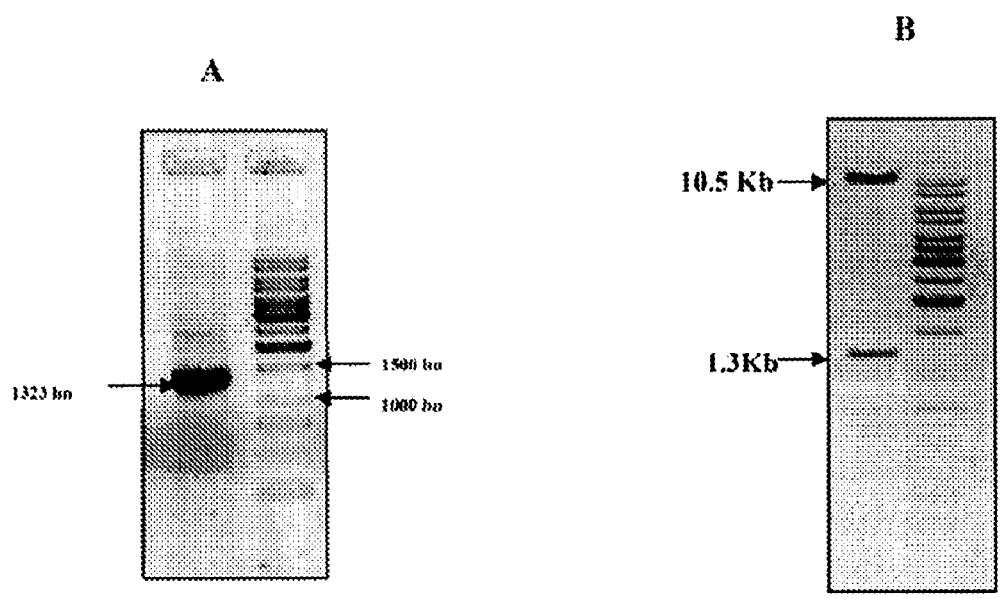
FIG. 5. A. Amplification of the ORF from the xylose Isomerase clone.

The ORF of the codon optimized Xylose Isomerase (XylA) gene in pSPORT was amplified with Forward primer (5' CTCTCTCGAGCAACCATGGGTGAATTCTTTCC 3') & the reverse primer (5'GAAACTCGAGCTTGTCGATTAAGAAATGTATTGGTT 3') containing the XhoI sites each. The amplified fragment was restricted with XhoI. pCAMBIA 1301 was simultaneously restricted with XhoI to release the hpt gene and the vector purified from agarose gel was ligated to the amplified fragment. Amplification of the ORF from the Xylose isomerase clone and the restriction of the pCAMBIA-XI with XhoI is represented in the FIG. 5

The ligation mix was transformed into DH10B. Transformed colonies were picked up and the plasmid isolated from these colonies amplified with XI primers and sequenced with the same. Thus constructs carrying the XI gene in the right orientation and right frame were identified. The sequence of the gene, cloned in the right frame, is given in the SEQ ID.4

The FIG. 6 represents the sequence of full-length codon optimized Xylose Isomerase transcript of SC-1 in frame in pCAMBIA vector and the replacement of hpt with XI in pCAMBIA-CO-XI. The hpt gene coding for hygromycin phospho transferase cloned between Xho-I sites of vector pCAMBIA1301 has been replaced by codon optimized Xylose isomerase in place of hygromycin has been named pCAMBIA-XI.

Example: 5

Transformation of Sunflower Using Xylose Isomerase as Positive Selection Marker

It is known that when genetic material is to be introduced into a population of cells by transformation, only a certain number of the cells are successfully transformed. Identification and selection of the transformed cells has traditionally been accomplished using negative selection, whereby transformed cells are capable of survival on media containing an agent which they are able to degrade, while non-transformed cells are killed on the media. Hygromycin is the most commonly used antibiotic while the hygromycin phospho transferase gene (hpt) in the construct used for transformation provides resistance to the transformed cells grown in media containing the antibiotic.

These negative selection methods have certain disadvantages. While the non-transformed cells may die because of the presence of antibiotics in the growth medium, they release toxins into the medium, which are inhibitory and toxic to the transformed cells as well. Moreover, the presence of an antibiotic resistance gene in ingested plants and microorganisms is a matter of concern for environmental groups and governmental authorities. In addition, selection of cells or tissues using negative selection requires precise timing of expression of the introduced genes in relation to the selection process. If the transgenic cells are treated with a toxic compound before the detoxifying gene is expressed or before enough gene products are produced to ameliorate the action of the toxic compound, both the transgenic and the non-transgenic cells are killed. If selection is delayed; the selection of transgenic cells or tissues may be hindered by, for example, shoot or callus formation from non-transgenic cells or tissues, which forms a barrier to the penetration of the compound used to select the transformed cells.

The above disadvantages are overcome to a substantial extent, by the method of positive selection, which makes it possible to selectively grow transformed cells without damaging or killing the non-transformed cells in the population and without introduction of antibiotic or herbicide resistance genes.

Many plant species do not have the innate ability to metabolise xylose and hence fail to thrive on media where xylose is the sole carbon source. Transformation of such species with constructs carrying xylose isomerase, as selection marker, would impart the transformed cells the ability to utilize xylose as the carbon source.

Transformation and Selection in Sunflower:

Plant Material:

For our study, we have used *Helianthus annuus* CMS234B—a maintainer line for 234A, an inbred line widely used as a female parent for production hybrid sunflower in India. It is a parental line of KBSH1 Hybrid, a national check, short duration variety (90-100 days) with oil content of 42% used as the maintainer line for all hybrid production.

Seeds of *Helianthus annuus* CMS 234B were dehusked and sterilised in 70% alcohol for 2 minutes and with 0.1% Mercuric Chloride for 4 minutes. The sterilized seeds were vigorously washed 4-5 times with sterile water, followed by imbibition in water for 2 hours at 25° C. in BOD. Three different explants viz., shoot apical meristem, Split embryonic axis and cotyledons were tested for their regeneration efficiency. Among these, the split embryonic axis (SEA) explants was found to have maximum potential for regeneration.

Isolation of Split Embryonic Axis Explant

After sterilization of the seed, the papery translucent seed coat and the thin transparent endosperm layer within was carefully peeled away. The first cut was made through the cotyledons parallel to the line where the two cotyledons are attached to dissect the shoot meristem. The primordial leaves from the tip of the shoot apical meristem were carefully cut away, if present. The tissue containing the root meristem was removed and the last cut was made directly through the center of the shoot apical meristem. Explants were collected on moistened filter paper.

Screening for Capability to Utilize Xylose as Carbon Source

In order to determine if sunflower is capable of using xylose as the carbon source, explants were cultured on regeneration media containing sucrose and xylose respectively.

100 SEA explants were isolated and cultured on Murashige and Skoog Medium (MS medium) containing 0.5 mg/l BAP where the carbon source was a) 3.5% sucrose; b) 3% Xylose; c) no carbon source for 3 weeks. The effect of the carbon source on the explant was observed at the end of 3 weeks.

FIG. 7 represents Sunflower SEA explants A) cultured on sucrose (35 gm/l) B) cultured on D-Xylose (30 gm/l) C) cultured on medium without any carbon source. The explants were photographed after 3 weeks.

Explants cultured in media containing xylose brown and die within 2-3 weeks. These explants look similar to explants grown in the absence of any carbon source in the medium. Thus, the sunflower CMS234B SEA explants do not appear to be able to use xylose as a carbon source.

Transformation of Sunflower using pCAMBIA-XI

Transfection with *Agrobacterium*

The seeds were sterilized and the split embryonic axis isolated as described earlier. *Agrobacterium tumefaciens* strain GV3101 harboring the binary vector pCAMBIA 1301 (carrying hpt gene) and the strain carrying vector pCAMBIA-XI were used for comparison.

*Agrobacterium* cells from the glycerol stock were grown overnight in Luria-Bertani (LB) medium containing Rifampicin (10 μg/ml), Gentamycin (10 μg/ml) and Kanamycin (50 μg/ml) and grown exponentially for a period of 4-6 hrs to reach O.D600=1.0. The cells were centrifuged at 6000 rpm for 5 min at 4° C. and then washed and resuspended in MS liquid to reach an $O.D_{600}$ of 1.0. The excised explants were immediately transferred to a vacuum infiltration flask containing 25 ml of the resuspended culture. Vacuum at 200 atm pressure for 15 min was applied and quickly released. The culture was then drained off completely and explants collected on a blotting paper. The explants were transferred to MS medium containing 0.5 mg/l BAP+2 gm/l sucrose) for 2 days at 26° C. under dark Example: 6

Selection and Regeneration

Positive Selection and Regeneration

After two days of co-cultivation, the explants were washed thoroughly with Murashige and Skoog (1972) liquid medium containing Cefotaxime 250 mg/l. The explants were then transferred to MS medium containing 0.5 mg/l BAP, 15 gm D-Xylose, 5 gm/l Sucrose, 250 mg/l Cefotaxime, 8 gm/l Agar, pH 5.6 and kept under photoperiod of 16 hr light and 8 hr dark condition for 3 weeks with two rounds of subculturing. After the selection period the shoots were subcultured onto Elongation medium containing ½ Strength MS medium. After 2 weeks the elongated shoots were transferred to Rooting medium (½ MS medium containing 0.01 mg/l IBA). The rooted plants were hardened for 2 days in water before transferring to soil and vermiculite mixture.

Negative Selection and Regeneration:

After two days of co cultivation the explants were washed thoroughly with MS medium containing 250 mg/l Cefotaxime. The explants were transferred to Selection and regeneration medium (MS medium containing 0.5 mg/l BAP, 15 mg/l Hygromycin, 250 mg/l Cefotaxime, 30 gm/l Sucrose, 8 gm/l Agar, pH 5.6). After the selection period the shoots were subcultured onto Elongation medium for 2 weeks (½ Strength MS medium). The elongated shoots were transferred to Rooting medium (½ Strength MS medium containing 0.01 mg/l IBA) and the rooted plants were subsequently transferred to soil.

Comparing Positive and Negative Selection:

Explants were transformed with pCAMBIA 1301 (with hpt) and pCAMBIA-XI (Xylose Isomerase replacing hpt) and selected on respective selection media containing different concentrations of hygromycin and xylose respectively. The explants surviving first selection were transferred for a second selection to the same medium for 21 days. Explants were subsequently transferred to their respective elongation media. Healthy shootlets were transferred to their respective rooting media.

The observations made are tabulated below:

A) Transformation of Explants with pCAMBIA-1301. Selection on Media Containing Hygromycin

| Conc. (mg/l) | No of explants infected | No. of explants surviving I selection (15 days) | No. of explants surviving I selection (21 days) | No. of explants surviving II selection (15 days) | No of PCR +ve explants | No. of explants Regenerating into shootlets | PCR +ve Regenerants |
|---|---|---|---|---|---|---|---|
| 30 | 100 | 45 | 22 | 12 | 12 | 1 | 1 |
| 25 | 100 | 50 | 30 | 17 | 15 | 3 | 2 |
| 20 | 100 | 58 | 42 | 28 | 20 | 5 | 2 |
| 15 | 100 | 65 | 50 | 43 | 27 | 7 | 3 |

B) Transformation of Explants with pCAMBIA-XI. Selection on Media Containing Xylose

TABLE 1

Transformation of sunflower SEA explants with pCAMBIA-1301 and pCAMBIA-XI

| Conc. (mg/l) | No of explants infected | No. of explants surviving I selection (15 days) | No. of explants surviving I selection (21 days) | No. of explants surviving II selection (15 days) | No of PCR +ve explants | No. of explants Regenerating into shootlets | PCR +ve Regenerants |
|---|---|---|---|---|---|---|---|
| 30 | 100 | 50 | 38 | 20 | 18 | 5 | 5 |
| 25 | 100 | 65 | 55 | 40 | 28 | 7 | 6 |
| 20 | 100 | 72 | 65 | 57 | 30 | 12 | 7 |
| 15 | 100 | 80 | 70 | 60 | 28 | 20 | 10 |

FIG. 8 represents Budding as observed in transformed SEA explants cultured on A) Hygromycin (25 mg/l) and B) Xylose (15 g/l)+Sucrose (5 gm/l) after 2 weeks of selection. Hygromycin appears to have a greater toxic effect on the explants than Xylose. The buds put forth by explants growing on Hygromycin media are seen to be stunted and hydric. They do not grow well and very few survive on elongation media. The regeneration efficiency is very low even at low concentrations of Hygromycin.

Better budding efficiencies are observed in explants selected on Xylose. More of the explants put forth normal shoot buds; these buds survive second selection better. 2-3 healthy shoots per explants are observed on positive selection as compared to 1-2 clustered and stunted shoots on Hygromycin medium. Plantlets grown on D-Xylose medium contained 90% green tissue when compared to plantlets grown on Hygromycin. The explants also show better survival and growth on elongation media. The buds are healthy and develop into shootlets in elongation media.

We observe 2-3 fold greater numbers of regenerating plantlets using XI as against the hpt for selection. Further improvement in the efficiency of regeneration is obtained when 5 g of sucrose and 15 g xylose was used in the selection medium following transfection. The following is the protocol standardized for the transformation and regeneration of sunflower using positive selection:

- Seeds of *Helianthus annuus* CMS 234B are dehusked and sterilised in 70% alcohol for 2 minutes followed by treatment with 0.1% Mercuric Chloride for 4 minutes.
- The sterilized seeds are vigorously washed 4-5 times with sterile water, followed by imbibition in water for 2 hours at 25° C. in BOD.
- The cotyledons, radicula and leaf primordial are carefully removed to expose the shoot apical meristem (SEA).
- The SEA explants are infected with Agrobacterial culture GV3101 carrying AGT-D15-XI (OD600=1.0)
- Vacuum infiltrated at 200 mbar for 15 min
- Cocultivation is done for two days on MS media containing 100 mg/l myoinositol, 0.5 mg/l BAP, 2 g/l Sucrose, 8 g/l Agar pH 5.6 for 2 days.
- The explants are washed for 15 min in MS media containing 35 g/l Sucrose, 100 mg/lmyoinositol, 250 mg/l Cefotaxime pH5.6 and blot dried.
- Subcultured onto MS media containing 100 mg/l myoinositol, 15 g/l xylose, 2 gm/l Sucrose, 0.5 mg/l BAP, 250 mg/l Cefotaxime, 8 g/l Agar, pH5.6 for 3 weeks
- Subcultured onto ½ MS media containing 50 mg/lmyoinositol, 15 g/l Sucrose, 250 mg/l Cefotaxime, 8 g/l Agar, pH5.6 for 1 week
- Subcultured onto ½MS media containing 50 mg/lmyoinositol, 0.01 mg/l IBA, 250 mg/l Cefotaxime, 8 g/l Agar pH 5.6
- The plantlets are finally transferred onto pots containing Red soil (10%) and vermiculite (90%) mixture.

Figure 9:
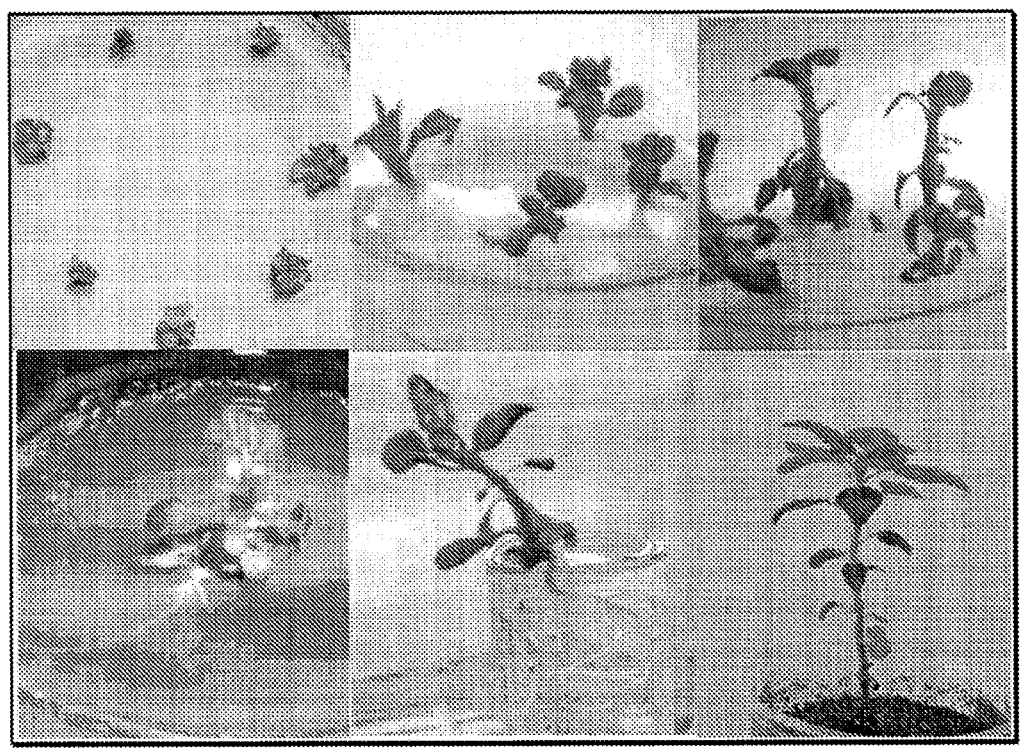

FIG. 9 represents A) SEA Explants on $I^{st}$ Selection Media. B) & C) Elongation Media D) Rooting Media E) & F) Plantlets in Hardening stage.

Starting with 100 explants, 2-3 transgenic plants carrying the hpt gene are obtained on transformation with pCAMBIA-1301. However, starting with the same number of explants, 12-15 transgenic plants carrying the M gene are obtained on transformation with pCAMBIA_XI, The plantlets obtained through Hygromycin selection are very few, moreover these plantlets are very weak and do not grow into a complete plants.

Example: 7

Molecular Analysis

Plantlets obtained after transformation were screened for the selectable marker gene by amplification with XI primers.

TABLE 2

Primers used for amplification of xylose isomerase genes.

Xylose Isomerase - Forward Primer   5' CTCTCTCGAGCAACCATGGGTGAATTCTTTCC 3'

Xylose Isomerase- Reverse Primer   5' GAAACTCGAGCTTGTCGATTAAGAAATGTATTGGTT-3'

Genomic DNA isolated from transformed plantlets were amplified with the above primers. The amplification conditions used were as follows:

DNA 100 ng
dNTP 200 μM
Primer 0.25 μM
$MgCl_2$ mM
10× Buffer 2.5 μl (Bangalore Genei)
Taq Polymerase 1 U
Total Volume 25 μl The cycling conditions used are as follows:
Amplifying Conditions Followed.

| | |
|---|---|
| 94° C.-3 min | |
| 94° C.-1 min | |
| 55° C.-1 min | ] 40 Cycles |
| 72° C.-1.3 min | |
| 72° C.-10 min | |

FIG. 10 represents the Amplification of transformed SEA explants with XI primers. 100 ng of genomic DNA of the selected plantlets, carrying pCAMBIA1301-XI were amplified with XI primers Lane 1-10: DNA samples from different explants; '+' Agrobacterium DNA; M: 1 kb ladder Note: Amplification in 9 explants with XI primers suggesting that these samples have XI integrated in their genome.

Ca. 90% of the selected explants show integration of the XI gene into their genome as seen by amplification of the XI gene in the transformed explants.

Thus, we report a stable transformation efficiency of 12-15% using xylose Isomerase for selection compared to the transformation efficiency of 0.2-6.2% reported with other selection markers around the world so far.

Thus, we prove that the use of xylose isomerase of SC1 for positive selection is an efficient method for transformation of sunflower explants. This selection system is more efficient and results in larger number of transgenic plants than traditional Kanamycin and Hygromycin based systems. It also solves the problem of raising transgenics from a recalcitrant crop like sunflower to produce transgenic sunflower successfully. Finally, it also fulfills the demand of alternative selective markers and avoids the use of antibiotic resistance genes in the development of genetically modified plants.

The invention claimed is:

1. A method for selecting and regenerating genetically transformed *Helianthus annuus* plant explants, comprising:
   a) constructing a recombinant vector that comprises a nucleic acid sequence operably linked to a regulatory sequence, the nucleic acid encoding an enzyme required for metabolizing a selection agent, the nucleic acid being isolated from Schizochytrium, the enzyme being xylose isomerase, and the selection agent being xylose;
   b) transforming *Helianthus annuus* plant explants with the recombinant vector using *agrobacterium*;
   c) selecting the *Helianthus annuus* plant explants transformed in b) on a growth medium containing xylose; and
   d) regenerating the *Helianthus annuus* plant explants selected in c).

2. The method according to claim 1, wherein the nucleic acid sequence has a sequence of SEQ ID NO: 1.

3. The method according to claim 2, wherein at least one of the nucleotides of the nucleic acid sequence is modified in that the expression of the modified nucleic acid sequence occurs in a host plant explant.

4. The method according to claim 3, wherein the modified nucleic acid sequence has a sequence of Seq ID NO: 3.

5. The method according to claim 2, wherein the nucleic acid sequence encodes a protein having a sequence of Seq ID NO: 2.

6. The method according to claim 1, wherein the regulatory sequence is a promoter sequence.

7. The method according to claim 4, wherein the expression of the nucleotide sequence in the transformed plant explants confers a metabolic advantage to the transformed explants as compared to that of non-transformed cells.

8. The method according to claim 4, wherein selecting the *Helianthus annuus* plant explants comprises selecting both the transformed and non-transformed plant explants based on a competitive metabolic advantage of utilizing xylose as a carbohydrate source attributed to the expression of the nucleic acid sequence.

9. The method according to claim 1, wherein a transformation efficiency obtained in b) is greater than or equal to 10%.

10. The method according to claim 1, wherein a transformation efficiency obtained in b) is greater than or equal to 15%.

11. The method according to claim 1, wherein the regeneration efficiency obtained in d) is 2-3 fold as compared to that of when the nucleic acid sequence is a hygromycin phosphotransferase gene rather than encoding the xylose isomerase and the selecting agent is hygromycin rather than xylose.

12. A method for selecting and regenerating genetically transformed *Helianthus annuus* plant explants, comprising:
   a) constructing a recombinant vector that comprises a nucleic acid sequence operably linked to a regulatory sequence, the nucleic acid encoding an enzyme required for metabolizing a selection agent, the nucleic acid having a sequence of SEQ ID NO: 1, the enzyme being xylose isomerase, and the selection agent being xylose;
   b) transforming *Helianthus annuus* plant explants with the recombinant vector using *agrobacterium*;
   c) selecting the *Helianthus annuus* plant explants transformed in b) on a growth medium containing xylose; and
   d) regenerating the *Helianthus annuus* plant explants selected in c).

* * * * *

SEQUENCE LISTING

```
<160> NUMBER OF SEQ ID NOS: 4

<210> SEQ ID NO 1
<211> LENGTH: 1323
<212> TYPE: DNA
<213> ORGANISM: Schizochytrium
<220> FEATURE:
<221> NAME/KEY: CDS
<222> LOCATION: (1)..(1323)

<400> SEQUENCE: 1 atg ggt gaa ttc ttt ccc gag gtt ggc aag att gaa tac aag gga cca        48
Met Gly Glu Phe Phe Pro Glu Val Gly Lys Ile Glu Tyr Lys Gly Pro
1               5                   10                  15 ggc agc aac gat gtg ctt tcg tac agg tgg tat aac cct gat gaa gag        96
Gly Ser Asn Asp Val Leu Ser Tyr Arg Trp Tyr Asn Pro Asp Glu Glu
            20                  25                  30 atc ctt gga aag aag atg aaa gac tgg ctt aag ttt tct gtc tgc ttt       144
Ile Leu Gly Lys Lys Met Lys Asp Trp Leu Lys Phe Ser Val Cys Phe
        35                  40                  45 tgg cat act ttc cga ggc gtc ggc atg gac ccc ttt ggc aaa cct acg       192
Trp His Thr Phe Arg Gly Val Gly Met Asp Pro Phe Gly Lys Pro Thr
    50                  55                  60 atc acc agc cgc ttc cag ggc gat gat gga tct gac tca gtc gaa aat       240
Ile Thr Ser Arg Phe Gln Gly Asp Asp Gly Ser Asp Ser Val Glu Asn
65                  70                  75                  80 gcg ctc cgt cgc gta gac gcc gcc ttt gag cta ttt aca aag ctt ggc       288
Ala Leu Arg Arg Val Asp Ala Ala Phe Glu Leu Phe Thr Lys Leu Gly
                85                  90                  95 gtt gag tac tac agc ttt cat gat gtg gat gtt tct ccc gaa ggt gca       336
Val Glu Tyr Tyr Ser Phe His Asp Val Asp Val Ser Pro Glu Gly Ala
            100                 105                 110 aca ctc aag gag aca aat gag aac ctt gac aag att acc gac cgc atg       384
Thr Leu Lys Glu Thr Asn Glu Asn Leu Asp Lys Ile Thr Asp Arg Met
        115                 120                 125 cta gaa ctg caa aag aaa aca gga gtg aag ctt ttg tgg ggt aca gct       432
Leu Glu Leu Gln Lys Lys Thr Gly Val Lys Leu Leu Trp Gly Thr Ala
    130                 135                 140 aac ctc ttt acc aac ccc cgc tac atg aac ggt ggc tcc acg aac ccg       480
Asn Leu Phe Thr Asn Pro Arg Tyr Met Asn Gly Gly Ser Thr Asn Pro
145                 150                 155                 160 gac ccg aat gtc ttc att cga gct gct gca cag gtt aaa aag gct atc       528
Asp Pro Asn Val Phe Ile Arg Ala Ala Ala Gln Val Lys Lys Ala Ile
                165                 170                 175
```

```
gat gtt acg cac aag ctt ggt ggt caa ggt ttt gta ttc tgg ggt ggt         576
Asp Val Thr His Lys Leu Gly Gly Gln Gly Phe Val Phe Trp Gly Gly
            180                 185                 190 cgc gaa ggc tac atg cac att ctc aac act gat gtt gtg cgt gag atg         624
Arg Glu Gly Tyr Met His Ile Leu Asn Thr Asp Val Val Arg Glu Met
                195                 200                 205 aac cac tat gcc cag atg ctg aag atg gcg att gca tac aag aag aag         672
Asn His Tyr Ala Gln Met Leu Lys Met Ala Ile Ala Tyr Lys Lys Lys
        210                 215                 220 atc ggc ttt gat ggt caa att ctt gtg gag cca aaa cct cgt gaa cca         720
Ile Gly Phe Asp Gly Gln Ile Leu Val Glu Pro Lys Pro Arg Glu Pro
225                 230                 235                 240 atg aag cac caa tat gat tac gat gta caa acc gtg att ggg ttc ttg         768
Met Lys His Gln Tyr Asp Tyr Asp Val Gln Thr Val Ile Gly Phe Leu
                245                 250                 255 cga gag cat ggg ctt gaa aaa gaa gtc ctg ctg aat gtt gaa ccc aac         816
Arg Glu His Gly Leu Glu Lys Glu Val Leu Leu Asn Val Glu Pro Asn
            260                 265                 270 cac acc cag ctt gcg ggc cac gaa ttt gag cat ggc ttt atc ttt gct         864
His Thr Gln Leu Ala Gly His Glu Phe Glu His Gly Phe Ile Phe Ala
        275                 280                 285 gcc aaa ctt ggc atg ctt gga agc att gat gct aat acc ggt tct gag         912
Ala Lys Leu Gly Met Leu Gly Ser Ile Asp Ala Asn Thr Gly Ser Glu
    290                 295                 300 agt ctt ggc tgg gac act gat gag ttc atc act gac cag act cat gcg         960
Ser Leu Gly Trp Asp Thr Asp Glu Phe Ile Thr Asp Gln Thr His Ala
305                 310                 315                 320 act ctg ctg tgt cgc acg att att gag atg ggc ggt ttc aaa aaa ggt        1008
Thr Leu Leu Cys Arg Thr Ile Ile Glu Met Gly Gly Phe Lys Lys Gly
                325                 330                 335 ggc ctt aac ttt gat gcc aag gtg cga cgc gaa agt act gat cca gag        1056
Gly Leu Asn Phe Asp Ala Lys Val Arg Arg Glu Ser Thr Asp Pro Glu
            340                 345                 350 gat ctc ttt atc gcg cac gtg gca tct atg gat gca ctt gct aaa ggt        1104
Asp Leu Phe Ile Ala His Val Ala Ser Met Asp Ala Leu Ala Lys Gly
        355                 360                 365 ctt cgc aat gct gcc aaa ttg gtt gat gaa ggc cgt atg gct aag atg        1152
Leu Arg Asn Ala Ala Lys Leu Val Asp Glu Gly Arg Met Ala Lys Met
    370                 375                 380 ctc gca gag cgc tac gct gga tgg gac tct gga cta ggt aag aga att        1200
Leu Ala Glu Arg Tyr Ala Gly Trp Asp Ser Gly Leu Gly Lys Arg Ile
385                 390                 395                 400 gag gat ggc cag agt tcg ctt gac gag ctg gag cat gcg ctc cag        1248
Glu Asp Gly Gln Ser Ser Leu Asp Glu Leu Glu His Ala Leu Gln
                405                 410                 415 aat gat gag gag ccc gct aag act tca gca aaa cag gag aag ttt att        1296
Asn Asp Glu Glu Pro Ala Lys Thr Ser Ala Lys Gln Glu Lys Phe Ile
            420                 425                 430 gct gtt ctc aac caa tac att tct taa                                    1323
Ala Val Leu Asn Gln Tyr Ile Ser
        435                 440

<210> SEQ ID NO 2
<211> LENGTH: 440
<212> TYPE: PRT
<213> ORGANISM: Schizochytrium

<400> SEQUENCE: 2

Met Gly Glu Phe Phe Pro Glu Val Gly Lys Ile Glu Tyr Lys Gly Pro
1               5                   10                  15
```

-continued

Gly Ser Asn Asp Val Leu Ser Tyr Arg Trp Tyr Asn Pro Asp Glu Glu
            20                  25                  30

Ile Leu Gly Lys Lys Met Lys Asp Trp Leu Lys Phe Ser Val Cys Phe
            35                  40                  45

Trp His Thr Phe Arg Gly Val Gly Met Asp Pro Phe Gly Lys Pro Thr
 50                  55                  60

Ile Thr Ser Arg Phe Gln Gly Asp Asp Gly Ser Asp Ser Val Glu Asn
 65                  70                  75                  80

Ala Leu Arg Arg Val Asp Ala Ala Phe Glu Leu Phe Thr Lys Leu Gly
                85                  90                  95

Val Glu Tyr Tyr Ser Phe His Asp Val Asp Val Ser Pro Glu Gly Ala
                100                 105                 110

Thr Leu Lys Glu Thr Asn Glu Asn Leu Asp Lys Ile Thr Asp Arg Met
            115                 120                 125

Leu Glu Leu Gln Lys Lys Thr Gly Val Lys Leu Leu Trp Gly Thr Ala
            130                 135                 140

Asn Leu Phe Thr Asn Pro Arg Tyr Met Asn Gly Gly Ser Thr Asn Pro
145                 150                 155                 160

Asp Pro Asn Val Phe Ile Arg Ala Ala Ala Gln Val Lys Lys Ala Ile
                165                 170                 175

Asp Val Thr His Lys Leu Gly Gly Gln Gly Phe Val Phe Trp Gly Gly
                180                 185                 190

Arg Glu Gly Tyr Met His Ile Leu Asn Thr Asp Val Arg Glu Met
            195                 200                 205

Asn His Tyr Ala Gln Met Leu Lys Met Ala Ile Ala Tyr Lys Lys Lys
    210                 215                 220

Ile Gly Phe Asp Gly Gln Ile Leu Val Glu Pro Lys Pro Arg Glu Pro
225                 230                 235                 240

Met Lys His Gln Tyr Asp Tyr Asp Val Gln Thr Val Ile Gly Phe Leu
                245                 250                 255

Arg Glu His Gly Leu Glu Lys Glu Val Leu Leu Asn Val Glu Pro Asn
            260                 265                 270

His Thr Gln Leu Ala Gly His Glu Phe Glu His Gly Phe Ile Phe Ala
        275                 280                 285

Ala Lys Leu Gly Met Leu Gly Ser Ile Asp Ala Asn Thr Gly Ser Glu
    290                 295                 300

Ser Leu Gly Trp Asp Thr Asp Glu Phe Ile Thr Asp Gln Thr His Ala
305                 310                 315                 320

Thr Leu Leu Cys Arg Thr Ile Ile Glu Met Gly Gly Phe Lys Lys Gly
                325                 330                 335

Gly Leu Asn Phe Asp Ala Lys Val Arg Arg Glu Ser Thr Asp Pro Glu
            340                 345                 350

Asp Leu Phe Ile Ala His Val Ala Ser Met Asp Ala Leu Ala Lys Gly
        355                 360                 365

Leu Arg Asn Ala Ala Lys Leu Val Asp Glu Gly Arg Met Ala Lys Met
    370                 375                 380

Leu Ala Glu Arg Tyr Ala Gly Trp Asp Ser Gly Leu Gly Lys Arg Ile
385                 390                 395                 400

Glu Asp Gly Gln Ser Ser Leu Asp Glu Leu Glu Glu His Ala Leu Gln
                405                 410                 415

Asn Asp Glu Glu Pro Ala Lys Thr Ser Ala Lys Gln Glu Lys Phe Ile
            420                 425                 430

Ala Val Leu Asn Gln Tyr Ile Ser
        435                 440

```
<210> SEQ ID NO 3
<211> LENGTH: 1323
<212> TYPE: DNA
<213> ORGANISM: Schizochytrium
<220> FEATURE:
<221> NAME/KEY: CDS
<222> LOCATION: (1)..(1323)

<400> SEQUENCE: 3 atg ggt gaa ttc ttt ccc gag gtt ggc aag att gaa tac aag gga cca      48
Met Gly Glu Phe Phe Pro Glu Val Gly Lys Ile Glu Tyr Lys Gly Pro
1               5                   10                  15 ggc agc aac gat gtg ctt tcg tac agg tgg tat aac cct gat gaa gag      96
Gly Ser Asn Asp Val Leu Ser Tyr Arg Trp Tyr Asn Pro Asp Glu Glu
            20                  25                  30 atc ctt gga aag aag atg aaa gac tgg ctt aag ttt tct gtc tgc ttt     144
Ile Leu Gly Lys Lys Met Lys Asp Trp Leu Lys Phe Ser Val Cys Phe
        35                  40                  45 tgg cat act ttc cga ggc gtc ggc atg gac ccc ttt ggc aaa cct acg     192
Trp His Thr Phe Arg Gly Val Gly Met Asp Pro Phe Gly Lys Pro Thr
    50                  55                  60 atc acc agc cgt ttc cag ggc gat gat gga tct gac tca gtc gaa aat     240
Ile Thr Ser Arg Phe Gln Gly Asp Asp Gly Ser Asp Ser Val Glu Asn
65                  70                  75                  80 gcg ctc cgt cgt gta gac gcc gcc ttt gag cta ttt aca aag ctt ggc     288
Ala Leu Arg Arg Val Asp Ala Ala Phe Glu Leu Phe Thr Lys Leu Gly
                85                  90                  95 gtt gag tac tac agc ttt cat gat gtg gat gtt tct ccc gaa ggt gca     336
Val Glu Tyr Tyr Ser Phe His Asp Val Asp Val Ser Pro Glu Gly Ala
            100                 105                 110 aca ctc aag gag aca aat gag aac ctt gac aag att acc gac cgt atg     384
Thr Leu Lys Glu Thr Asn Glu Asn Leu Asp Lys Ile Thr Asp Arg Met
        115                 120                 125 cta gaa ctg caa aag aaa aca gga gtg aag ctt ttg tgg ggt aca gct     432
Leu Glu Leu Gln Lys Lys Thr Gly Val Lys Leu Leu Trp Gly Thr Ala
    130                 135                 140 aac ctc ttt acc aac ccc cgt tac atg aac ggt ggc tcc acg aac ccg     480
Asn Leu Phe Thr Asn Pro Arg Tyr Met Asn Gly Gly Ser Thr Asn Pro
145                 150                 155                 160 gac ccg aat gtc ttc att cga gct gct gca cag gtt aaa aag gct atc     528
Asp Pro Asn Val Phe Ile Arg Ala Ala Ala Gln Val Lys Lys Ala Ile
                165                 170                 175 gat gtt acg cac aag ctt ggt ggt caa ggt ttt gta ttc tgg ggt ggt     576
Asp Val Thr His Lys Leu Gly Gly Gln Gly Phe Val Phe Trp Gly Gly
            180                 185                 190 cgt gaa ggc tac atg cac att ctc aac act gat gtt gtg cgt gag atg     624
Arg Glu Gly Tyr Met His Ile Leu Asn Thr Asp Val Val Arg Glu Met
        195                 200                 205 aac cac tat gcc cag atg ctg aag atg gcg att gca tac aag aag aag     672
Asn His Tyr Ala Gln Met Leu Lys Met Ala Ile Ala Tyr Lys Lys Lys
    210                 215                 220 atc ggc ttt gat ggt caa att ctt gtg gag cca aaa cct cgt gaa cca     720
Ile Gly Phe Asp Gly Gln Ile Leu Val Glu Pro Lys Pro Arg Glu Pro
225                 230                 235                 240 atg aag cac caa tat gat tac gat gta caa acc gtg att ggg ttc ttg     768
Met Lys His Gln Tyr Asp Tyr Asp Val Gln Thr Val Ile Gly Phe Leu
                245                 250                 255 cga gag cat ggg ctt gaa aaa gaa gtc ctg ctg aat gtt gaa ccc aac     816
Arg Glu His Gly Leu Glu Lys Glu Val Leu Leu Asn Val Glu Pro Asn
            260                 265                 270
```

-continued

```
cac acc cag ctt gcg ggc cac gaa ttt gag cat ggc ttt atc ttt gct      864
His Thr Gln Leu Ala Gly His Glu Phe Glu His Gly Phe Ile Phe Ala
        275                 280                 285 gcc aaa ctt ggc atg ctt gga agc att gat gct aat acc ggt tct gag      912
Ala Lys Leu Gly Met Leu Gly Ser Ile Asp Ala Asn Thr Gly Ser Glu
    290                 295                 300 agt ctt ggc tgg gac act gat gag ttc atc act gac cag act cat gcg      960
Ser Leu Gly Trp Asp Thr Asp Glu Phe Ile Thr Asp Gln Thr His Ala
305                 310                 315                 320 act ctg ctg tgt cgt acg att att gag atg ggc ggt ttc aaa aaa ggt     1008
Thr Leu Leu Cys Arg Thr Ile Ile Glu Met Gly Gly Phe Lys Lys Gly
                325                 330                 335 ggc ctt aac ttt gat gcc aag gtg cga cgt gaa agt act gat cca gag     1056
Gly Leu Asn Phe Asp Ala Lys Val Arg Arg Glu Ser Thr Asp Pro Glu
            340                 345                 350 gat ctc ttt atc gcg cac gtg gca tct atg gat gca ctt gct aaa ggt     1104
Asp Leu Phe Ile Ala His Val Ala Ser Met Asp Ala Leu Ala Lys Gly
        355                 360                 365 ctt cgt aat gct gcc aaa ttg gtt gat gaa ggc cgt atg gct aag atg     1152
Leu Arg Asn Ala Ala Lys Leu Val Asp Glu Gly Arg Met Ala Lys Met
    370                 375                 380 ctc gca gag cgt tac gct gga tgg gac tct gga cta ggt aag aga att     1200
Leu Ala Glu Arg Tyr Ala Gly Trp Asp Ser Gly Leu Gly Lys Arg Ile
385                 390                 395                 400 gag gat ggc cag agt tcg ctt gac gag ctg gag cat gcg ctc cag         1248
Glu Asp Gly Gln Ser Ser Leu Asp Glu Leu Glu His Ala Leu Gln
                405                 410                 415 aat gat gag gag ccc gct aag act tca gca aaa cag gag aag ttt att     1296
Asn Asp Glu Glu Pro Ala Lys Thr Ser Ala Lys Gln Glu Lys Phe Ile
            420                 425                 430 gct gtt ctc aac caa tac att tct taa                                 1323
Ala Val Leu Asn Gln Tyr Ile Ser
        435                 440

<210> SEQ ID NO 4
<211> LENGTH: 1323
<212> TYPE: DNA
<213> ORGANISM: Schizochytrium
<220> FEATURE:
<221> NAME/KEY: CDS
<222> LOCATION: (1)..(1323)

<400> SEQUENCE: 4 atg ggt gaa ttc ttt ccc gag gtt ggc aag att gaa tac aag gga cca       48
Met Gly Glu Phe Phe Pro Glu Val Gly Lys Ile Glu Tyr Lys Gly Pro
1               5                  10                  15 ggc agc aac gat gtg ctt tcg tac agg tgg tat aac cct gat gaa gag       96
Gly Ser Asn Asp Val Leu Ser Tyr Arg Trp Tyr Asn Pro Asp Glu Glu
            20                  25                  30 atc ctt gga aag aag atg aaa gac tgg ctt aag ttt tct gtc tgc ttt      144
Ile Leu Gly Lys Lys Met Lys Asp Trp Leu Lys Phe Ser Val Cys Phe
        35                  40                  45 tgg cat act ttc cga ggc gtc ggc atg gac ccc ttt ggc aaa cct acg      192
Trp His Thr Phe Arg Gly Val Gly Met Asp Pro Phe Gly Lys Pro Thr
    50                  55                  60 atc acc agc cgt ttc cag ggc gat gat gga tct gac tca gtc gaa aat      240
Ile Thr Ser Arg Phe Gln Gly Asp Asp Gly Ser Asp Ser Val Glu Asn
65                  70                  75                  80 gcg ctc cgt cgt gta gac gcc gcc ttt gag cta ttt aca aag ctt ggc      288
Ala Leu Arg Arg Val Asp Ala Ala Phe Glu Leu Phe Thr Lys Leu Gly
                85                  90                  95 gtt gag tac tac agc ttt cat gat gtg gat gtt tct ccc gaa ggt gca      336
```

-continued

| | | | | | | | | | | | | | | | |
|---|---|---|---|---|---|---|---|---|---|---|---|---|---|---|---|
| Val | Glu | Tyr | Tyr | Ser | Phe | His | Asp | Val | Asp | Val | Ser | Pro | Glu | Gly | Ala |
| | | | 100 | | | | 105 | | | | 110 | | | | |

```
aca ctc aag gag aca aat gag aac ctt gac aag att acc gac cgt atg       384
Thr Leu Lys Glu Thr Asn Glu Asn Leu Asp Lys Ile Thr Asp Arg Met
        115                 120                 125 cta gaa ctg caa aag aaa aca gga gtg aag ctt ttg tgg ggt aca gct       432
Leu Glu Leu Gln Lys Lys Thr Gly Val Lys Leu Leu Trp Gly Thr Ala
    130                 135                 140 aac ctc ttt acc aac ccc cgt tac atg aac ggt ggc tcc acg aac ccg       480
Asn Leu Phe Thr Asn Pro Arg Tyr Met Asn Gly Gly Ser Thr Asn Pro
145                 150                 155                 160 gac ccg aat gtc ttc att cga gct gct gca cag gtt aaa aag gct atc       528
Asp Pro Asn Val Phe Ile Arg Ala Ala Ala Gln Val Lys Lys Ala Ile
                165                 170                 175 gat gtt acg cac aag ctt ggt ggt caa ggt ttt gta ttc tgg ggt ggt       576
Asp Val Thr His Lys Leu Gly Gly Gln Gly Phe Val Phe Trp Gly Gly
            180                 185                 190 cgt gaa ggc tac atg cac att ctc aac act gat gtt gtg cgt gag atg       624
Arg Glu Gly Tyr Met His Ile Leu Asn Thr Asp Val Val Arg Glu Met
        195                 200                 205 aac cac tat gcc cag atg ctg aag atg gcg att gca tac aag aag aag       672
Asn His Tyr Ala Gln Met Leu Lys Met Ala Ile Ala Tyr Lys Lys Lys
    210                 215                 220 atc ggc ttt gat ggt caa att ctt gtg gag cca aaa cct cgt gaa cca       720
Ile Gly Phe Asp Gly Gln Ile Leu Val Glu Pro Lys Pro Arg Glu Pro
225                 230                 235                 240 atg aag cac caa tat gat tac gat gta caa acc gtg att ggg ttc ttg       768
Met Lys His Gln Tyr Asp Tyr Asp Val Gln Thr Val Ile Gly Phe Leu
                245                 250                 255 cga gag cat ggg ctt gaa aaa gaa gtc ctg ctg aat gtt gaa ccc aac       816
Arg Glu His Gly Leu Glu Lys Glu Val Leu Leu Asn Val Glu Pro Asn
            260                 265                 270 cac acc cag ctt gcg ggc cac gaa ttt gag cat ggc ttt atc ttt gct       864
His Thr Gln Leu Ala Gly His Glu Phe Glu His Gly Phe Ile Phe Ala
        275                 280                 285 gcc aaa ctt ggc atg ctt gga agc att gat gct aat acc ggt tct gag       912
Ala Lys Leu Gly Met Leu Gly Ser Ile Asp Ala Asn Thr Gly Ser Glu
    290                 295                 300 agt ctt ggc tgg gac act gat gag ttc atc act gac cag act cat gcg       960
Ser Leu Gly Trp Asp Thr Asp Glu Phe Ile Thr Asp Gln Thr His Ala
305                 310                 315                 320 act ctg ctg tgt cgt acg att att gag atg ggc ggt ttc aaa aaa ggt      1008
Thr Leu Leu Cys Arg Thr Ile Ile Glu Met Gly Gly Phe Lys Lys Gly
                325                 330                 335 ggc ctt aac ttt gat gcc aag gtg cga cgt gaa agt act gat cca gag      1056
Gly Leu Asn Phe Asp Ala Lys Val Arg Arg Glu Ser Thr Asp Pro Glu
            340                 345                 350 gat ctc ttt atc gcg cac gtg gca tct atg gat gca ctt gct aaa ggt      1104
Asp Leu Phe Ile Ala His Val Ala Ser Met Asp Ala Leu Ala Lys Gly
        355                 360                 365 ctt cgt aat gct gcc aaa ttg gtt gat gaa ggc cgt atg gct aag atg      1152
Leu Arg Asn Ala Ala Lys Leu Val Asp Glu Gly Arg Met Ala Lys Met
    370                 375                 380 ctc gca gag cgt tac gct gga tgg gac tct gga cta ggt aag aga att      1200
Leu Ala Glu Arg Tyr Ala Gly Trp Asp Ser Gly Leu Gly Lys Arg Ile
385                 390                 395                 400 gag gat ggc cag agt tcg ctt gac gag ctg gag gag cat gcg ctc cag      1248
Glu Asp Gly Gln Ser Ser Leu Asp Glu Leu Glu Glu His Ala Leu Gln
                405                 410                 415 aat gat gag gag ccc gct aag act tca gca aaa cag gag aag ttt att      1296
```

```
Asn Asp Glu Glu Pro Ala Lys Thr Ser Ala Lys Gln Glu Lys Phe Ile
            420                 425                 430 gct gtt ctc aac caa tac att tct taa                              1323
Ala Val Leu Asn Gln Tyr Ile Ser
        435                 440
```